United States Patent [19]
Jojima et al.

[11] 4,056,617
[45] Nov. 1, 1977

[54] ORGANIC PYRIDAZYL PHOSPHOROTHIOATES AND THEIR USE AS INSECTICIDES

[75] Inventors: Teruomi Jojima; Hideakira Tsuji, both of Tokyo; Shinjiro Yamamoto; Teiji Omino, both of Shiga, all of Japan

[73] Assignee: Sankyo Company Limited, Tokyo, Japan

[21] Appl. No.: 620,227

[22] Filed: Oct. 6, 1975

Related U.S. Application Data

[60] Continuation of Ser. No. 540,234, Jan. 10, 1975, abandoned, Division of Ser. No. 67,292, Aug. 26, 1970, abandoned.

[30] Foreign Application Priority Data

Sept. 17, 1969 Japan .................. 44-73788
Sept. 1, 1969 Japan .................. 44-69218

[51] Int. Cl.² .............................. A01N 9/36
[52] U.S. Cl. ................................. 424/200
[58] Field of Search ......................... 424/200

[56] References Cited
U.S. PATENT DOCUMENTS 3,100,206  8/1963  Rigterink ............... 260/250 A
3,878,210  4/1975  Lorenz et al. ........... 424/250

Primary Examiner—V. D. Turner
Attorney, Agent, or Firm—Toren, McGeady and Stanger

[57] ABSTRACT

New organic phosphorus compounds having the formula

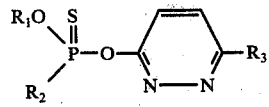

wherein $R_1$ represents an alkyl group of 1-4 carbon atoms, $R_2$ represents an alkoxy group of 1-4 carbon atoms or phenyl group and $R_3$ represents hydrogen atom, an alkyl group of 1-4 carbon atoms, phenyl group or the group of the formula $-X-R_4$ in which $R_4$ represents an alkyl group of 1-6 carbon atoms or a benzyl group which may be substituted with a halogen atom in the phenyl moiety and X represents oxygen atom or sulfur atom. The present compounds are prepared by reacting a phosphoric or phosphonic acid halide having the formula

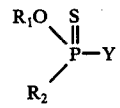

wherein $R_1$ and $R_2$ are as defined above and Y represents a halogen atom with a pyridazinone derivative having the formula

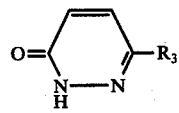

wherein $R_3$ is as defined above. The present compounds show a superior insecticidal activity against various harmful insects, e.g., rice stem borers, planthoppers, mites, aphids, flies, mosquitoes and the like and thus they are useful as an insecticide or acaricide.

48 Claims, No Drawings

ORGANIC PYRIDAZYL PHOSPHOROTHIOATES AND THEIR USE AS INSECTICIDES

CROSS REFERENCES TO RELATED APPLICATIONS

This application is a continuation of copending application Ser. No. 540,234, filed on Jan. 10, 1975, now abandoned, which in turn was a division of application Ser. No. 67,292, filed on Aug. 26, 1970, now abandoned.

This invention relates to a new class of organic phosphorus compounds, process for the preparation thereof and their use as an insecticide or acaricide.

More particularly, it is concerned with an organic phosphorus compound having the formula

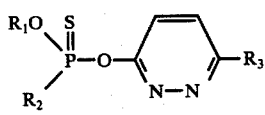

wherein $R_1$ represents an alkyl group of 1–4 carbon atoms, $R_2$ represents an alkoxy group of 1–4 carbon atoms or phenyl group and $R_3$ represents hydrogen atom, an alkyl group of 1–4 carbon atoms, phenyl group or the group of the formula

—X—R$_4$ in which $R_4$ represents an alkyl group of 1–6 carbon atoms or a benzyl group which may be substituted with a halogen atom in the phenyl moiety and X represents oxygen atom or sulfur atom, with a process for the preparation thereof as well as with an insecticidal and acaricidal composition containing the same as an active ingredient and a method for controlling harmful insects by utilizing the same.

In the above formula (I), the group $R_1$ may be illustrated by methyl, ethyl, n-propyl, isopropyl, n-butyl, isobutyl or tert.butyl; the group $R_2$ may be illustrated by methoxy, ethoxy, isopropoxy, n-butoxy, isobutoxy, tert.butoxy or phenyl; the group $R_3$ may be illustrated by hydrogen, methyl, ethyl, n-propyl, tert.butyl, phenyl, methoxy, ethoxy, n-propoxy, isopropoxy, n-butoxy, sec.butoxy, isobutoxy, tert.butoxy, pentyloxy, hexyloxy, methylthio, ethylthio, n-propylthio, isopropylthio, n-butylthio, sec. butylthio, isobutylthio, tert.butylthio, pentylthio, hexylthio, benzyloxy, benzylthio, o-, m- or p-fluorobenzyloxy, o-, m- or p-chlorobenzylthio, o-, m- or p-bromobenzylthio or o-, m- or p-fluorobenzylthio.

Heretofore, a number of organic phosphorus compounds of various types have been synthesized and evaluated for insecticidal activities and many organic phosphorus compounds are now commercially available as an insecticide, including, for example, parathion, methyl parathion, E.P.N. (Registered Trade Mark, O-Ethyl O-p-nitrophenylphenylphosphonothioate), malathion, diazinon and the like.

Such prio insecticidal phosphorus compounds have still, however, some shortcomings to be improved, for example, in that they are not equally effective against all kinds of harmful insects. For instance, some prior phosphorus compounds are known effective against certain kinds of harmful insects, e.g., rice stem borers, planthoppers and the like, but not so effective against many mites and aphids.

Thus, many attempts have been made in the art to discover and develop universally effective insecticidal phosphorus compounds.

As a result of our extensive investigations on the preparation of various roganic phosphorus compounds and the insecticidal activity thereof, it has been found that a new type of the organic phosphorus compounds of the above formula (I) is successfully synthesized and they exhibit high insecticidal and acaricidal activity against various harmful insects as compared with prior analogous phosphorus compounds.

It is, accordingly, an object of this invention to provide new organic phosphorus compounds of the above formula (I) which are highly effective for controlling harmful insects.

It is another object of this invention to provide a process for the preparation of the valuable organic phosphorus compounds of the above formula (I).

It is another object of this invention to provide a new method for controlling harmful insects which comprises applying the new phosphorus compound of the above formula (I) to harmful insects.

Still another object of this invention is to provide an insecticidal and acaricidal composition which comprises as an active ingredient the new phosphorus compound of the above formula (I) and an agriculturally-acceptable carrier.

These and other objects of this invention will become apparent to those skilled in the art from the following description.

The new organic phosphorus compound (I) of this invention can be easily prepared by reacting a phosphoric or phosphonic acid halide having the formula

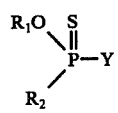

wherein $R_1$ and $R_2$ are as defined above and Y represents a halogen atom with a pyridazinone derivative having the formula

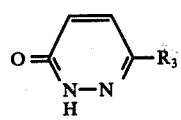

wherein $R_3$ is as defined above.

In carrying out the process of this invention, the reaction can be usually and preferably effected by admixing the starting halide of the above formula (II) with the pyridazinone derivative of the above formula (III) in the presence or absence of a solvent and then either maintaining the resulting mixture at room temperature or heating said mixture up to about 70° C. Examples of a suitable solvent which may be employed in the process of this invention include inert organic solvents, e.g., ether, acetone, methyl ethyl ketone, benzene, toluene, xylene, acetonitrile and the like and water. The reagent, the pyridazinone derivative of the above formula (III), may be employed in the reaction as a free base, but it is preferable for the better proceeding of the reaction that, where the free base is employed in the reaction, the reaction be effected in the presence of an acid-binding agent. Examples of a suitable acid-binding agent include inorganic bases such as alkali metal hydroxides or carbonates, e.g., sodium hydroxide or potassium carbonate; organic bases such as alkali metal alcoholates, e.g., sodium methylate or ethylate, cyclic amines, e.g., pyridine, or alkylamines, e.g., triethylamine or diethylamine; and the like. It is also preferable for the better proceeding of the reaction that the reagent be employed in the reaction as the previously-formed alkali metal salt thereof.

After completion of the reaction, the reaction product (I) can be readily recovered and purified from the reaction mixture by a conventional method. For instance, the reaction mixture is filtered to remove inorganic salts and the filtrate is concentrated. To the residue (crude end product) is added an aqueous alkali solution, e.g., aqueous sodium hydroxide or aqueous sodium carbonate and the resulting mixture is extracted with a suitable water-immiscible organic solvent, e.g., benzene, toluene or chloroform. The organic layer is separated and washed thoroughly with water and then the solvent is distilled off and, if necessary, column-chromatographed to give the pure end product (I).

Illustrative of the preferred group of the organic phosphorus compounds (I) of this invention are as follows:

1. O,O-Diethyl O-3-pyridazylphosphorothioate;
2. O,O-diethyl O-(6-methyl-3-pyridazyl)phosphoro thioate;
3. O,O-diethyl O-(6-phenyl-3-pyridazyl)phosphoro thioate;
4. O,O-diethyl O-(6-methylthio-3-pyridazyl)phosphorothioate;
5. O,O-diethyl O-(6-ethylthio-3-pyridazyl)phosphorothioate;
6. O,O-diethyl O-(6-isopropylthio-3-pyridazyl)phosphorothioate;
7. O,O-diethyl O-(6-benzylthio-3-pyridazyl)phosphorothioate;
8. O,O-diethyl O-(6-p-chlorobenzylthio-3-pyridazyl)-phosphorothioate;
9. O,O-diethyl O-(6-methoxy-3-pyridazyl)phosphorothioate;
10. O,O-diisopropyl O-(6-methylthio-3-pyridazyl)phosphorothioate;
11. O,O-diisobutyl O-(6-methylthio-3-pyridazyl)phosphorothioate;
12. O-ethyl O-(6-methylthio-3-pyridazyl)phenylphosphonothioate;
13. O-ethyl O-(6-n-butylthio-3-pyridazyl)phenylphosphonothioate;
14. O,O-di-n-butyl O-(6-methylthio-3-pyridazyl)phosphorothioate;
15. O,O-diisopropyl O-(6-ethylthio-3-pyridazyl)phosphorothioate;
16. O,O-diethyl O-(6-n-butylthio-3-pyridazyl)phosphorothioate;
17. O,O-di-n-butyl O-(6-n-butylthio-3-pyridazyl)phosphorothioate;
18. O,O-diisopropyl O-(6-n-butylthio-3-pyridazyl)phosphorothioate;
19. O-ethyl O-(6-methoxy-3-pyridazyl)phenylphosphonothioate;
20. O,O-diisopropyl O-(6-methoxy-3-pyridazyl)phosphorothioate;
21. O,O-di-n-butyl O-(6-methoxy-3-pyridazyl)phosphorothioate;
22. O,O-diethyl O-(6-ethoxy-3-pyridazyl)phosphorothioate;
23. O,O-diisopropyl O-(6-ethoxy-3-pyridazyl)phosphorothioate;
24. O,O-diethyl O-(6-isopropoxy-3-pyridazyl)phosphorothioate;
25. O,O-diethyl O-(6-n-propoxy-3-pyridazyl)phosphorothioate;
26. O,O-diethyl O-(6-n-butoxy-3-pyridazyl)phosphorothioate;
27. O,O-diisopropyl O-(6-n-butoxy-3-pyridazyl)phosphorothioate;
28. O,O-di-n-butyl O-(6-n-butoxy-3-pyridazyl)phosphorothioate;
29. O-ethyl O-(6-n-butoxy-3-pyridazyl)phenylphosphonothioate;
30. O,O-diethyl O-(6-isobutoxy-3-pyridazyl)phosphorothioate;
31. O,O-diethyl O-(6-n-pentoxy-3-pyridazyl)phosphorothioate;
32. O,O-diethyl O-[6-(3-methyl-n-butoxy)-3-pyridazyl]-phosphorothioate;
33. O,O-diethyl O-(6-n-hexyloxy-3-pyridazyl)phosphorothioate;
34. O,O-dimethyl O-(6-n-butylthio-3-pyridazyl)phosphorothioate;
35. O,O-diemethyl O-(6-isobutoxy-3-pyridazyl)phosphorothioate;
36. O,O-diethyl O-(6-sec.butoxy-3-pyridazyl)phosphorothioate;
37. O,O-diethyl O-(6-tert.butoxy-3-pyridazyl)phosphorothioate;
38. O,O-diethyl O-(6-benzyloxy-3-pyridazyl)phosphorothioate; and
39. O,O-dimethyl O-(6-isopropoxy-3-pyridazyl)phosphorothioate.

The pyridazinone derivatives of the above formula (III) which may be employed as a reagent in the process of this invention are new substances except for those derivatives of the above formula (III) wherein $R_3$ represents hydrogen, methyl, phenyl, methoxy or methylthio. Such new substances can be readily prepared, for example, by heating the corresponding 3-halo-6-alkoxy (or benzyloxy)pyridazine together with anhydrous potassium acetate and acetic acid at about 120°–150° C in a sealed tube, by heating a 6-halopyridazinone together with the corresponding alkyl(or benzyl)mercaptan in an alcohol in the presence of a base at about 100°–150° C in a sealed tube, or by reacting the corresponding ω-acyl propionic acid with hydrazine hydrate to form the corresponding 6-alkyl-4,5-dihydro-3(2H)-pyridazinone and then oxidizing the resulting product with selenium dioxide.

In another aspect of this invention, there is provided a method for controlling harmful insects which comprises contacting said insects with an insecticidally effective amount of the organic phosphorus compound of the above formula (I) and also an insecticidal and acaricidal composition which comprises as an active ingredient the organic phosphorus compound of the above formula (I) and an agriculturally-acceptable carrier.

The active compound (I) used according to this invention may be conveniently formulated by a known procedure and employed in various forms including liquids, dusts, granules and wettable powders etc.

Liquids may be prepared by dissolving the active compound in an agriculturally-acceptable liquid carrier, i.e. a suitable solvent with or without one or more of known adjuvants commonly employed in the art such as emulsifying agents, wetting agents, or dispersing agents. Suitable solvents include water, alcohols such as methanol or ethanol, acetone, benzene, toluene, xylene, solvent naphtha, petroleum ether, the mixture thereof and the like. Suitable adjuvants may be any of those which is ordinarily employed in the art, and include, for example, the condensation products of alkylene oxides with phenols or organic acids, alkylarylsulfonates, dialkyl sulfosuccinate, polyoxyethylene ether or ester derivatives of alcohols or acids and the like.

Dusts and granules may be prepared by mixing said active compound in an inert agriculturally acceptable solid carrier by a conventional procedure. Suitable solid carriers for use in this invention include, for example, talc, pyrophylite, kieselguhr, clay, bentonite, diatomaceous earth, kaolin, precipitated chalk and the like.

Wettable powders may be prepared by mixing said active compound with one or more of the aforementioned solid carriers and suitable dispersing agents. Suitable dispersing agents include, for example, those aforementioned adjuvants such as alkylbenzenesulfonates, lignosulfontes or polyoxyalkylene glycol ethers or esters.

The concentration of the active compound in the composition of this invention may normally be from about 0.1 to about 95% by weight, and preferably from about 0.5 to about 70% by weight, based upon the total weight of the composition, although the amount of the active ingredient employed will largely depend upon such factors as the degree of insect damage, the form of a composition or the particular active compound, toxicity of the active compound and the like. It should be, however, understood that the amount of an active compound employed is not critical feature of this invention. Two or more of said active ingredients may be conveniently incorporated into the agricultural insecticidal composition of this invention.

The agricultural insecticidal and acaricidal composition of this invention may also include other known insecticidal agents, e.g., benzenehexachloride, 1,1,1-trichloro-2,2-bis (p-chlorophenyl)ethane, 0,0-dimethyl S-(N-methylcarbamoylmethyl)phosphorodithioate, 0,0-diethyl S-2-(ethylthio)ethyl phosphorodithioate and the like; fungicidal agents e.g., phenylmercurychloride, kasugamycin, zinc ethylenebisdithiocarbamate, manganese ethylenebisdithiocarbamate, ferric methylarsonate, N-trichloromethylthio-4-cyclohexane-1,2-dicarboxyimide, and the like; fertilizers, and the like.

The method for controlling harmful insects of this invention comprises contacting said insects with an insecticidally effective amount of the active compound (I). The active compound is, of course, to be applied in such an amount sufficient to exert the desired insecticidal effect, usually in a concentration of about 5 ppm or higher for liquid preparations, e.g. liquids and diluted wettable powders and in a dose rate of about 7–50 g. of the active compound per 10 ares for solid preparations, e.g., dusts and granules.

The active compound (I) of this invention has been found to be highly effective for controlling various harmful insects, e.g. mosquitoes, flies, rice borers, rice leafhoppers, rice maggots, planthoppers, aphids, mites, cutworms, spider mites and the like.

In order to demonstrate the excellent insecticidal and acaricidal activity of the organic phosphorus compound (I) according to this invention, the insecticidal and acaricidal tests and the results therefrom are shown hereinbelow.

All parts and percentages in the Experiments and herein are by weight unless otherwise stated.

EXPERIMENT 1

Test for Acaricidal Activity of the Organic Phosphorus Compounds of this Invention Against Two-Spotted Spider Mite (*Tetranychus Urticae*)

A wettable powder was prepared by homogeneously admixing and pulverizing 20 parts of each of the indicated test compounds, 3 parts of sodium dodecylbenzenesulfonate, 2 parts of polyvinyl alcohol and 75 parts of clay. The wettable powder thus prepared was diluted with water to the indicated concentration and then 0.01% of a spreader ["Gramin", Trade name of a spreader available from Nihon Nyukazai K.K., Japan, containing polyoxyethylene dodecyl ether, polyoxyethylene aryl ether sulfonic acid and abietic acid polyalcohol ester] was added thereto.

Into the diluted wettable powder thus prepared was dipped for 10 seconds leaves of cowpea (*Vigna sinensis*) upon which adult two-spotted spider mites lived. After air-drying, the leaves were left in a room maintained at 25° C. After 24 hours, mortality of mite (%) was investigated. An average number of the mites which were employed in this test was 50 mites for each test.

The results are summarized in the following Table I.

Table I

| Test compound No.* | Mortality of mite (%) | |
| --- | --- | --- |
| | 100 ppm | 10 ppm |
| 1 | 80.3 | 15.5 |
| 2 | 100 | 100 |
| 3 | 100 | 100 |
| 4 | 100 | 100 |
| 5 | 100 | 100 |
| 6 | 100 | 86.0 |
| 7 | 85.2 | 35.0 |
| 8 | 100 | 68.0 |
| 9 | 100 | 92.0 |
| 10 | 92.4 | 41.1 |
| 11 | 81.3 | 47.5 |
| 12 | 100 | 100 |
| 13 | 100 | 100 |
| 14 | 100 | 100 |
| 15 | 100 | 100 |
| 16 | 100 | 100 |
| 17 | 80.0 | 16.0 |
| 18 | 100 | 100 |

*The number of the test compound is the same as specified hereinabove.

EXPERIMENT 2

Test for Insecticidal Activity of the Organic Phosphorus Compounds of this Invention Against Turnip Aphid (*Rhopalosiphum Pseudobrassicae*)

The test compound indicated below was formulated and diluted as set forth in the above Experiment 1.

Into the diluted wettable powder thus prepared were dipped for 30 seconds leaves of radish (*Raphanus sativus*) upon which turnip aphids lived. After air-drying, the leaves, which were put into a small bottle filled with water together with a cotton stopper, were placed into a glass cylinder. Then, the leaves were left while maintaining at 25° C. After 24 hours, mortality of aphid (%) was investigated.

The test aphids were employed at a rate of 50 insects for each test.

The results are summarized in the following Table II.

Table II

| Test compound No.* | Mortality of aphid (%) | |
|---|---|---|
| | 100 ppm | 30 ppm |
| 1 | 98 | 30 |
| 2 | 100 | 100 |
| 3 | 100 | 84 |
| 4 | 100 | 100 |
| 5 | 100 | 100 |
| 6 | 100 | 100 |
| 7 | 100 | 96 |
| 8 | 100 | 78 |
| 9 | 100 | 100 |
| 10 | 100 | 100 |
| 11 | 92 | 28 |
| 12 | 100 | 100 |

*The number of the test compound is the same as specified hereinabove.

EXPERIMENT 3

Test for Insecticidal Activity of the Organic Phosphorus Compounds of this Invention Against Brown Planthopper (*Nilaparvata Lugens*)

The test compound indicated below was formulated and diluted as set forth in the above Experiment 1.

The diluted wettable powder thus prepared was applied by spraying to rice plants which were planted in an unglazed pot with a diameter of 9 cm. in an amount of 10 ml. per pot. Immediately after the sprayed wettable powder was air-dried, the plants were covered with a glass cylinder having a diameter of 7 cm. and a height of 14 cm. Into the above-mentioned glass cylinder were placed the planthoppers at a rate of 15 insects per pot. Thereafter, the upper opening of the glass cylinder was closed with a wire netting cover. After the pot was kept at 25° C for 24 hours, mortality of hopper (%) was investigated.

The results are summarized in the following Table III.

Table III

| Test compound No.* | Mortality of hopper (%) | |
|---|---|---|
| | 100 ppm | 500 ppm |
| 1 | 100 | 96.6 |
| 2 | 100 | 93.3 |
| 3 | 66.6 | 16.6 |
| 4 | 100 | 100 |
| 5 | 100 | 100 |
| 6 | 100 | 100 |
| 7 | 70.0 | 23.3 |
| 8 | 76.6 | 23.3 |
| 9 | 100 | 100 |
| 10 | 100 | 100 |
| 11 | 100 | 96.6 |
| 12 | 100 | 100 |
| 13 | 96.6 | 66.6 |
| 14 | 100 | 100 |
| 15 | 100 | 100 |
| 16 | 100 | 100 |
| 17 | 100 | 100 |
| 18 | 100 | 100 |

*The number of the test compound is the same as specified hereinabove.

EXPERIMENT 4

Test for Insecticidal Activity of the Organic Phosphorus Compounds of this Invention Against American Cockroach (*Periplaneta Americana*)

The test compound indicated below was dissolved in acetone and the resulting solution was deposited at the dose indicated below on the bottom of a 20 ml. volume jar having a diameter of 24 mm. and a depth of 44 mm. After evaporation of the solvent, 10 insects (1st instar larvae), within 4 days at 27° C after hatching, were introduced into the test jar. Then, the jar was covered with a polyethylene cap and kept at 25° C. Two test jars were used for each dose. After 24 hours, mortality of insect (%) was investigated.

The results are summarized in the following Table IV.

Table IV

| Test compound No. | Mortality of insect (%) Dose per jar | | |
|---|---|---|---|
| | 100 μg. | 10 μg. | 1 μg. |
| 1 | 100 | 100 | 100 |
| 2 | 100 | 100 | 100 |
| 3 | 100 | 100 | 100 |
| 4 | 100 | 100 | 100 |
| 11 | 100 | 90 | 0 |
| 12 | 100 | 100 | 90 |
| 13 | 100 | 100 | 30 |
| 15 | 100 | 100 | 100 |
| 16 | 100 | 100 | 100 |
| 17 | 100 | 10 | 0 |
| 18 | 100 | 100 | 75 |
| 20 | 100 | 100 | 100 |
| 21 | 100 | 20 | 0 |
| 23 | 100 | 100 | 100 |
| 24 | 100 | 100 | 100 |
| 25 | 100 | 100 | 20 |
| 26 | 100 | 100 | 95 |
| 30 | 100 | 100 | 15 |
| 31 | 100 | 100 | 100 |
| 32 | 100 | 100 | 100 |
| 33 | 100 | 100 | 0 |

*The number of the test compound is the same as specified hereinabove.

It will be apparent from the above results that the organic phosphorus compounds (I) of this invention exhibit excellent insecticidal and acaricidal activities against a wide variety of harmful insects.

The following examples are given for the purpose of illustrating of this invention, but they should not be construed to be limiting the scope of this invention.

EXAMPLE 1

0,0-Diethyl 0-(6-methylthio-3-pyridazyl)phosphorothioate

To a solution of 6 g. of 6-methylthio-3(2H)-pyridazinone and 5.5 g. of triethylamine in 40 ml. of acetonitrile was added dropwise, while stirring and maintaining under anhydrous condition at room temperature 7.9 of 0,0-diethylthiophosphoric acid chloride. Then, the temperature of the resulting mixture was raised up to 50° C and the stirring was continued at that temperature for additional 6 hours. After being allowed to stand at room temperature overnight, the reaction mixture was filtered to remove inorganic salts, and the filtrate was concentrated under reduced pressure. To the residue was added an 5% aqueous sodium hydroxide solution and the resulting mixture was extracted twice with benzene. The combined benzene extracts were washed with water, dried over anhydrous sodium sulfate and the solvent was distilled off to give yellow oily substance. The substance was dissolved in a small amount of carbon tetrachloride, the resulting solution was adsorbed upon an alumina column, elution was effected with carbon tetrachloride and then the solvent was distilled off to give the desired product as colorless needles, which was then recrystallized from n-hexane to show a melting point of 63°-64° C.

Analysis for $C_9H_{15}N_2O_3S_2P$ : Calculated: C, 37.63%; H, 5.14%; N, 9.52%; P, 10.52%. Found: C, 37.12%; H, 5.23%; N, 9.99%; P, 9.99%.

Following the substantially same procedure as set forth above, there were produced the following organic phosphorus compounds:

0,0-Diisopropyl 0-(6-methylthio-3-pyridazyl)phosphorothioate, m.p. 56° C.

Analysis for $C_{11}H_{19}N_2O_3S_2P$: Calculated: C, 41.11%; H, 5.96%; N, 8.72%; P, 9.64%. Found: C, 40.88%; H, 5.90%; N, 8.61%; P, 9.42%.

0,0-diisobutyl 0-(6-methylthio-3-pyridazyl)phosphorothioate, m.p. 52° C.

Analysis for $C_{13}H_{23}N_2O_3S_2P$: Calculated: C, 44.56%; H, 6.62%; N, 7.99%; P, 8.84%. Found: C, 44.55%; H, 6.70%; N, 7.91%; P, 8.98%.

0,0-diethyl 0-(6-isopropylthio-3-pyridazyl)phosphorothioate, yellow oil

Analysis for $C_{11}H_{19}N_2O_3S_2P$: Calculated: C, 40.98%; H, 5.94%; N, 8.69%; P, 9.61%. Found: C, 41.13%; H, 6.03%; N, 8.76%; P, 9.90%.

0,0-diethyl 0-(6-benzylthio-3-pyridazyl)phosphorothioate, m.p. 76° C.

Analysis for $C_{15}H_{19}N_2O_3S_2P$: Calculated: C, 46.91%; H, 5.34%; N, 7.82%; P, 8.64%. Found: C, 47.94%; H, 5.20%; N, 7.87%; P, 7.96%.

0,0-diethyl 0-(6-p-chlorobenzylthio-3-pyridazyl)-phosphorothioate, m.p. 71° C.

Analysis for $C_{15}H_{14}ClN_2O_3S_2P$ Calculated: C, 42.80%; H, 4.62%; N, 7.13%; P, 7.88%. Found: C, 42.51%; H, 4.60%; N, 6.80%; P, 8.12%.

0,0-diethyl 0-(6-methoxy-3-pyridazyl)phosphorothioate, m.p. 33°–35° C.

Analysis for $C_9H_{11}N_2O_4SP$: Calculated: C, 38.85%; H, 5.43%; N, 10.07%; P, 11.13%. Found: C, 38.50%; H, 5.40%; N, 9.91%; P, 12.00%.

EXAMPLE 2

0,0-Diethyl 0-(6-ethylthio-3-pyridazyl)phosphorothioate

To a solution of 0.74 g. of metallic sodium in 40 ml. of absolute methanol was added 5 g. of 6-ethylthio-3(2H)-pyridazinone and the resulting mixture was stirred at room temperature for 2 hours to form the corresponding sodium salt. Thereafter, the methanol was distilled off under reduced pressure and the residue was suspended in dry acetonitrile. To the suspension was added dropwise with stirring 7 g. of 0,0-diethylthiophosphoric acid chloride. The resulting mixture was heated to 50° C, stirred at that temperature for additional 6 hours and then allowed to stand at room temperature overnight.

After completion of the reaction, the reaction mixture was filtered to remove inorganic salts and the filtrate was treated in the same manner as in the above Example 1 to give 7 g. of the desired product as colorless needles melting at 33°–35° C.

Analysis for $C_{10}H_{17}N_2O_3S_2P$: Calculated: C, 39.08%; H, 5.58%; N, 9.11%; P, 10.08%. Found: C, 38.80%; H, 5.50%; N, 8.91%; P, 9.90%.

EXAMPLE 3

0,0-Diethyl 0-(6-n-butylthio-3-pyridazyl)phosphorothioate

The same procedure as in the above Example 2 was repeated except that there were employed 1.51 g. of potassium hydroxide instead of the metallic sodium as a base to give 9 g. of the desired product as pale yellow oily substance. $n_D^{26}$ 1.5318

Analysis for $C_{12}H_{21}N_2O_3S_2P$: Calculated: C, 42.84%; H, 6.29%; N, 8.33%; P, 9.21%. Found: C, 42.67%; H, 6.66%; N, 8.30%; P, 8.86%.

Following the substantially same procedure as set forth above, there were produced the following organic phosphorus compounds:

0-ethyl 0-(6-n-butylthio-3-pyridazyl)phenylphosphonothioate, $n_D^{26}$ 1.5844;

0,0-di-n-butyl 0-(6-methylthio-3-pyridazyl)phosphorothioate, $n_D^{26}$ 1.5152;

0,0-diisopropyl O-(6-ethylthio-3-pyridazyl)phosphorothioate, $n_D^{23}$ 1.5106;

O,O-di-n-butyl O-(6-n-butylthio-3-pyridazyl)phosphorothioate, $n_D^{26}$ 1.5116;

O,O-diisopropyl O-(6-n-butylthio-3-pyridazyl)phosphorothioate, $n_D^{26}$ 1.5194;

O-ethyl O-(6-methoxy-3-pyridazyl)phenylphosphonothioate, m.p. 82°–83° C;

O,O-diisopropyl O-(6-methoxy-3-pyridazyl)phosphorothioate, $n_D^{27}$ 1.4977;

O,O-di-n-butyl O-(6-methoxy-3-pyridazyl)phosphorothioate, $n_D^{27}$ 1.4958;

O,O-diisopropyl O-(6-ethoxy-3-pyridazyl)phosphorothioate, $n_D^{25}$ 1.4952;

O,O-diethyl O-(6-isopropoxy-3-pyridazyl)phosphorothioate, $n_D^{27}$ 1.4997;

O,O-dimethyl O-(6-isopropoxy-3-pyridazyl)phosphorothioate, $n_D^{23.5}$ 1.5115;

O,O-diethyl O-(6-n-propoxy-3-pyridazyl)phosphorothioate, $n_D^{27}$ 1.5013;

O-ethyl O-(6-n-butoxy-3-pyridazyl)phenylphosphonothioate, $n_D^{23.5}$ 1.5543;

O,O-diethyl O-(6-n-butoxy-3-pyridazyl)phosphorothioate, $n_D^{24}$ 1.5006;

O,O-dimethyl O-(6-isobutoxy-3-pyridazyl)phosphorothioate, $n_D^{23.5}$ 1.5073;

O,O-diethyl O-(6-isobutoxy-3-pyridazyl)phosphorothioate, $n_D^{27}$ 1.4933;

O,O-diethyl O-(6-n-pentoxy-3-pyridazyl)phosphorothioate, $n_D^{24}$ 1.4983;

O,O-diethyl O-[6-(3-methyl-n-butoxy)-3-pyridazyl]-phosphorothioate, $n_D^{24}$ 1.4975; and O,O-diethyl O-(6-n-hexyloxy-3-pyridazyl)phosphorothioate, $n_D^{22.5}$ 1.4978.

EXAMPLE 4

O-Ethyl O-(6-methylthio-3-pyridazyl)phenylphosphonothioate

The same procedure as in the above Example 1 was repeated except that there were employed 12 g. of O-ethyl thionobenzene phosphonic acid chloride instead of the O,O-diethylthiophosphoric acid chloride to give 15.5 g. of the desired product as pale yellow oily substance, which solidified after being allowed to stand at ambient temperature for a while. The solid was then recrystallized from n hexane to give the pure product as colorless needles melting at 55°–56° C.

Analysis for $C_{13}H_{15}N_2O_2S_2P$: Calculated: C, 47.84%; H, 4.63%; N, 8.58%; P, 9.49%. Found: C, 47.60%; H, 4.50%, N, 8.51%; P, 9.10%.

EXAMPLE 5

Five parts of O,O-diethyl O-(6-methylthio-3-pyridazyl)-phosphorothioate was homogeneously mixed and pulverized together with 95 parts of clay to give a dust. The dust thus prepared was applied to crops by spraying on the stems and leaves thereof at a rate of 3–4 kg./10 ares by means of a conventional sprayer.

EXAMPLE 6

Twenty parts of O-ethyl O-(6-methylthio-3-pyridazyl)phenylphosphonothioate, 3 parts of sodium dodecylbenzenesulfonate, 2 parts of polyvinyl alcohol and 75 parts of clay were homogeneously mixed and pulverized to give a wettable powder. The wettable powder thus prepared was diluted with water to a 500–1,000 times volume and applied to crops by spraying in a conventional manner.

What is claimed is:

1. An insecticidal composition which comprises a carrier and as an active ingredient an effective amount of O,O-diethyl O-(6-n-propoxy-3-pyridazyl)phosphorothioate.

2. An insecticidal composition which comprises a carrier and as an active ingredient an effective amount of O,O-diethyl O-(6-n-pentoxy-3-pyridazyl)phosphorthioate.

3. An insecticidal composition which comprises a carrier and as an acitive ingredient an effective amount of O,O-diethyl O-(6-n-hexyloxy-3-pyridazyl)phosphorothioate.

4. An insecticidal composition which comprises a carrier and as an active ingredient an effective amount of O,O-diethyl O-(6-isobutoxy-3-pyridazyl)phosphorothioate.

5. An insecticidal composition which comprises a carrier and as an active ingredient an effective amount of O,O-diethyl O-[6-(3-methyl-n-butoxy)-3-pyridazyl] phosphorothioate.

6. An insecticidal composition which comprises a carrier and as an active ingredient an effective amount of O,O-diethyl O-(6-isopropoxy-3-pyridazyl)phosphorothioate.

7. An insecticidal composition which comprises a carrier and as an active ingredient an effective amount of O,O-diethyl O-(6-n-butoxy-3-pyridazyl) phosphorothioate.

8. An insecticidal composition which comprises a carrier and as an active ingredient an effective amount of O,O-diethyl O-(6-ethoxy-3-pyridazyl) phosphorothioate.

9. An insecticidal composition which comprises a carrier and as an active ingredient an effective amount of O,O-diisopropyl O-(6-ethoxy-3-pyridazyl)phosphorothioate.

10. An insecticidal composition which comprises a carrier and as an active ingredient an effective amount of O,O-diethyl O-(6-methylthio-3-pyridazyl)phosphorothioate.

11. An insecticidal composition which comprises a carrier and as an active ingredient an effective amount of O,O-diisopropyl O-(6-methylthio-3-pyridazyl)phosphorothioate.

12. An insecticidal composition which comprises a carrier and as an active ingredient an effective amount of O,O-di-n-butyl O-(6-methylthio-3-pyridazyl) phosphorothioate.

13. An insecticidal composition which comprises a carrier and as an active ingredient an effective amount of O,O-diethyl O-(6-ethylthio-3-pyridazyl)phosphorothioate.

14. An insecticidal composition which comprises a carrier and as an active ingredient an effective amount of O,O-diisopropyl O-(6-ethylthio-3-pyridazyl)phosphorothioate.

15. An insecticidal composition which comprises a carrier and as an active ingredient an effective amount of O,O-diethyl O-(6-isopropylthio-3-pyridazyl)phosphorothioate.

16. An insecticidal composition which comprises a carrier and as an active ingredient an effective amount of O,O-diethyl O-(6-n-butylthio-3-pyridazyl)phosphorothioate.

17. An insecticidal composition which comprises a carrier and as an active ingredient an effective amount of O,O-diisopropyl O-(6-n-butylthio-3-pyridazy)phosphorothioate.

18. An insecticidal composition which comprises a carrier and as an active ingredient an effective amount of O,O-di-n-butyl O-(6-n-butylthio-3-pyridazyl)phosphorothioate.

19. A method for controlling harmful insects which comprises contacting said insects with an insecticidally effective amount of O,O-diethyl O-(6-n-propoxy-3-pyridazyl) phosphorothioate.

20. A method for controlling harmful insects which comprises contacting said insects with an insecticidally effective amount of O,O-diethyl O-(6-n-pentoxy-3-pyridazyl) phosphorothioate.

21. A method for controlling harmful insects which comprises contacting said insects with an insecticidally effective amount of O,O-diethyl O-(6-n-hexyloxy-3-pyridazyl) phosphorothioate.

22. A method for controlling harmful insects which comprises contacting said insects with an insecticidally effective amount of O,O-diethyl O-(6-isobuotxy-3-pyridazyl) phosphorothioate.

23. A method for controlling harmful insects which comprises contacting said insects with an insecticidally effective amount of O,O-diethyl O-[6-(3-methyl-n-butoxy)-3-pyridazyl]-phosphorothioate.

24. A method for controlling harmful insects which comprises contacting said insects with an insecticidally effective amount of O,O-diethyl O-(6-isopropoxy-3-pyridazyl) phosphorothioate.

25. A method for controlling harmful insects which comprises contacting said insects with an insecticidally effective amount of O,O-diethyl O-(6-n-butoxy-3-pyridazyl) phosphorothioate.

26. A method for controlling harmful insects which comprises contacting said insects with an insecticidally effective amount of O,O-diethyl O-(6-ethoxy-3-pyridazyl) phosphorothioate.

27. A method for controlling harmful insects which comprises contacting said insects with an insecticidally effective amount of O,O-diisopropyl O-(6-ethoxy-3-pyridazy) phosphorothioate.

28. A method for controlling harmful insects which comprises contacting said insects with an insecticidally effective amount of O,O-diethyl O-(6-methylthio-3-pyridazyl) phosphorothioate.

29. A method for controlling harmful insects which comprises contacting said insects with an insecticidally effective amount of O,O-diisopropyl O-(6-methylthio-3-pyridazyl) phosphorothioate.

30. A method for controlling harmful insects which comprises contacting said insects with an insecticidally effective amount of O,O-di-n-butyl O-(6-methylthio-3-pyridazyl) phosphorothioate.

31. A method for controlling harmful insects which comprises contacting said insects with an insecticidally effective amount of O,O-diethyl O-(6-ethylthio-3-pyridazyl) phosphorothioate.

32. A method for controlling harmful insects which comprises contacting said insects with an insecticidally effective amount of O,O-diisopropyl O-(6-ethylthio-3-pyridazyl) phosphorothioate.

33. A method for controlling harmful insects which comprises contacting said insects with an insecticidally effective amount of O,O-diethyl O-(6-isopropylthio-3-pyridazyl) phosphorothioate.

34. A method for controlling harmful insects which comprises contacting said insects with an insecticidally effective amount of O,O-diethyl O-(6-n-butylthio-3-pyridazyl) phosphorothioate.

35. A method for controlling harmful insects which comprises contacting said insects with an insecticidally effective amount of O,O-diisopropyl O-(6-n-butylthio-3-pyridazyl) phosphorothioate.

36. A method for controlling harmful insects which comprises contacting said insects with an insecticidally effective amount of O,O-di-n-butyl O-(6-n-butylthio-3-pyridazyl)phosphorothioate.

37. A method for controlling harmful mites which comprises contacting said mites with an acaricidally effective amount of O,O-diethyl O-(6-n-propoxy-3-pyridazyl)phosphorothioate.

38. A method for controlling harmful mites which comprises contacting said mites with an acaricidally effective amount of O,O-diethyl O-(6-n-pentoxy-3-3-pyridazyl)phosphorothioate.

39. A method for controlling harmful mites which comprises contacting said mites with an acaricidally effective amount of O,O-diethyl O-(6-n-hexyloxy-3-pyridazyl) phosphorothioate.

40. A method for controlling harmful mites which comprises contacting said mites with an acaricidally effective amount of O,O-diethyl O-(6-isobutoxy-3-pyridazyl) phosphorothioate.

41. A method for controlling harmful mites which comprises contacting said mites with an acaricidally effective amount of O,O-diethyl O-[6-(3-methyl-n-butoxy)-3-pyridazyl]phosphorothioate.

42. A method for controlling harmful mites which comprises contacting said mites with an acaricidally effective amount of O,O-diethyl O-(6-isopropoxy-3-pyridazyl) phosphorothioate.

43. A method for controlling harmful mites which comprises contacting said mites with an acaricidally effective amount of O,O-diethyl O-(6-n-butoxy-3-pyridazyl)phosphorothioate.

44. A method for controlling harmful mites which comprises contacting said mites with an acaricidally effective amount of O,O-diethyl O-(6-ethoxy-3-pyridazyl)phosphorothioate.

45. A method for controlling harmful mites whcih comprises contacting said mites with an acaricidally effective amount of O,O-diethyl O-(6-methylthio-3-pyridazyl)phosphorothioate.

46. A method for controlling harmful mites which comprises contacting said mites with an acaricidally effective amount of O,O-diethyl O-(6-ethylthio-3-pyridazyl) phosphorothioate.

47. A method for controlling harmful mites which comprises contacting said mites with an acaricidally effective amount of O,O-diethyl O-(6-isopropylthio-6-pyridazyl) phosphorothioate.

48. A method for controlling harmful mites which comprises contacting said mites with an acaricidally effective amount of O,O-diethyl O-(6-n-butylthio-3-pyridazyl) phosophorothioate.

* * * * *